United States Patent [19]

Zhou et al.

[11] Patent Number: 5,214,227
[45] Date of Patent: May 25, 1993

[54] LOW PRESSURE DEHYDROGENATION OF LIGHT PARAFFINS

[75] Inventors: Ying Zhou, State College, Pa.; Stephen M. Davis, Baton Rouge, La.

[73] Assignee: Exxon Research & Engineering Company, Florham Park, N.J.

[21] Appl. No.: 811,392

[22] Filed: Dec. 20, 1991

[51] Int. Cl.$^5$ .............................................. C07C 5/333
[52] U.S. Cl. ..................................................... 585/660
[58] Field of Search ........................................ 585/660

[56] References Cited

U.S. PATENT DOCUMENTS 3,972,806  8/1976  Antos ................................... 585/660
4,056,576  11/1977  Gregory et al. .................... 585/660
4,080,394  3/1978  Antos ................................... 585/660

Primary Examiner—Asok Pal
Attorney, Agent, or Firm—Penny L. Prater; Henry E. Naylor

[57] ABSTRACT

A process for the dehydrogenation of light alkanes which employs a gallium/platinum catalyst on a magnesium/alumina spinel support. The catalyst comprises 0.3 to 5 wt. % Ga and 0.1 to 5 wt. % Pt on a spinel type support material characterized by the formula $Mg_xAl_2O_{3+x}$ where x is a number from about 0.1 to 1.1. A water soluble Mg salt is incorporated into this support prior to the impregnation of Pt and Ga.

11 Claims, 1 Drawing Sheet

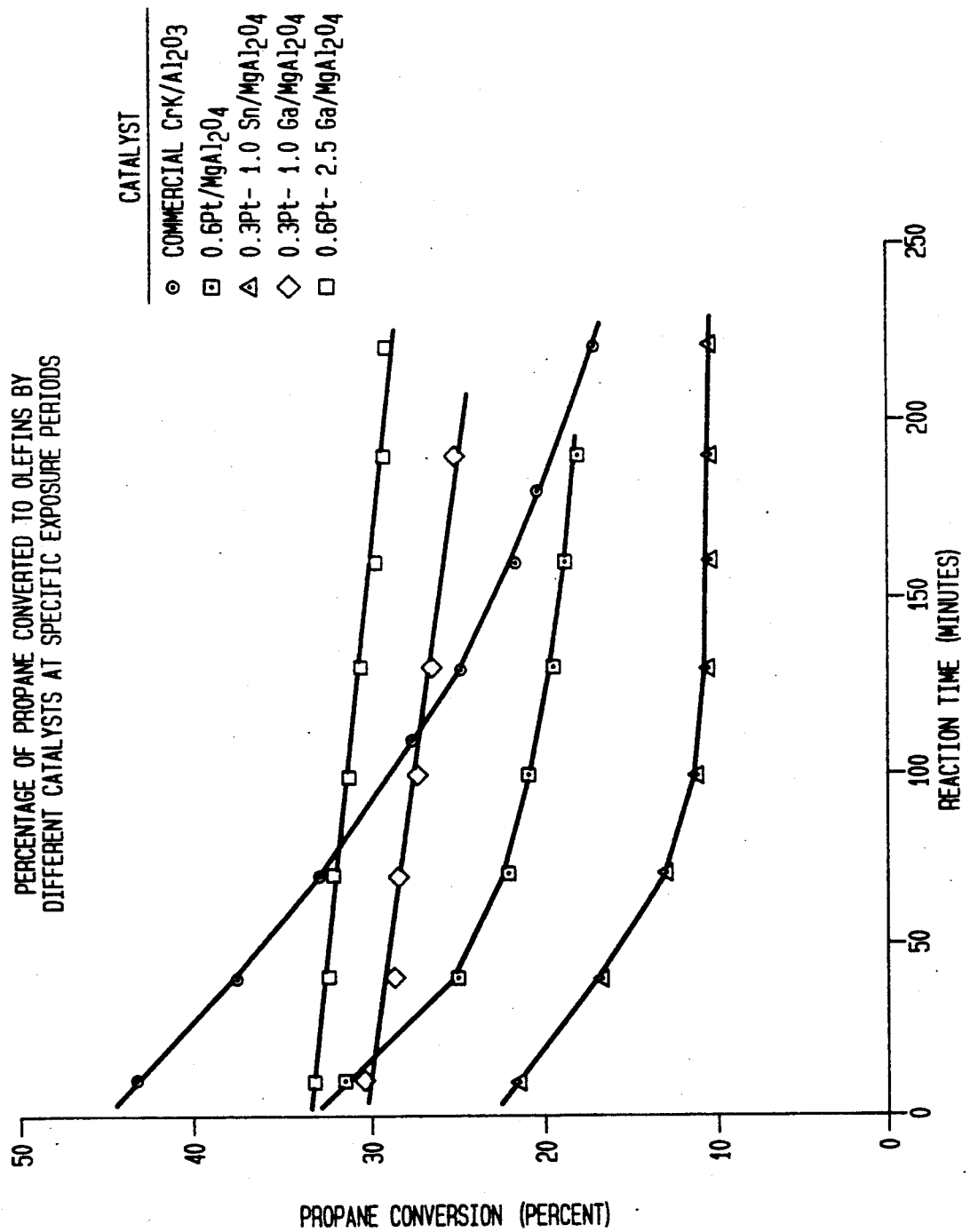

LOW PRESSURE DEHYDROGENATION OF LIGHT PARAFFINS

FIELD OF THE INVENTION

This invention relates to a process for the dehydrogenation of light alkanes which employs a gallium/platinum catalyst on a magnesium/alumina support. Copending U.S. patent application Ser. No. 07/811,393, filed on the same date as the present application, relates to the preparation of this catalyst.

BACKGROUND OF THE INVENTION

The most frequently employed dehydrogenation reactions involve the dehydrogenation of alkylcyclohexanes to aromatics; however, light alkane dehydrogenation is increasingly being employed. The reason for this is the growing enthusiasm for low emissions gasoline. The light alkane dehydrogenation process normally involves conversion of propane, butanes, or pentanes to the corresponding olefins, and the process configurations are similar to those utilized in catalytic reforming. As compared to catalytic reforming, the light alkane dehydrogenation processes typically operate at higher temperatures and lower pressures and with more frequent catalyst regeneration.

One of the best known methods for light alkane dehydrogenation is the so-called oxidative dehydrogenation process. In this process the light alkanes are reacted with oxygen over a suitably prepared mixed metal oxide catalyst to produce a mixture of olefin, water, $CO_2$, and unreacted alkane. While high conversions combined with high olefin selectivities can be achieved, this process has a number of disadvantages including loss of fuel value due to water and $CO_2$ formation and process operations that are costly and difficult from the viewpoint of industrial hazards associated with exothermic combustion reactions.

A more direct and preferred approach is direct dehydrogenation over a suitable catalyst to produce olefins and molecular hydrogen. This chemistry has recently received considerable interest, although high reaction temperatures in the range of 500°–650° C. are required to obtain a significant equilibrium yield (e.g., 15-50 wt. %) of olefin. Moreover, under these reaction conditions, light alkanehydrogenolysis to methane and ethane is a competing, undesirable reaction. Most catalysts studied to date have not shown very high selectivities for dehydrogenation versus hydrogenolysis or have suffered from rapid catalyst deactivation necessitating frequent regeneration. As a consequence, the process economics have not been clearly favorable. Large incentives exist for catalysts which show improved resistance to deactivation and that may be regenerated using simple procedures such as air treatment.

Prior art catalysts for direct dehydrogenation of light paraffins are mostly based on platinum on support materials such as silica, alumina, modified aluminas, and zeolites. Frequently, alkali and/or alkali earth oxide additives are included to improve stability and/or selectivity for olefin production relative to methane and ethane. One family of prior art dehydrogenation catalysts contain platinum and tin dispersed on an alumina support modified to contain alkali and/or alkali earth metals. U.S. Pat. No. 4,430,517, for example, discloses light paraffin dehydrogenation catalysts comprising a platinum group component, a Group IVA component, especially tin, an alkali or alkaline earth component, more than 0.2 wt. % of a halogen component, and a porous carrier material, wherein the atomic ratio of the alkali or alkaline earth component to the platinum group component is at least 10. Preferably, the catalyst comprises about 1 to 3 wt. % potassium. The classic Houdry-type catalyst described in UK Patent Application GB 2162082A employs chromium and potassium dispersed on alumina. By contrast, European Patent Application 212,850 discloses light paraffin dehydrogenation with catalysts containing a platinum group component on a silicalite support which is substantially free of alkali or alkali earth metals.

U.S. Pat. No. 4,547,618 discloses propane dehydrogenation catalysts comprising ZSM-12 zeolite modified with platinum and magnesium or manganese. Gallium has been noted as an important component in dehydrocyclodimerization catalysts for selective conversion of $C_3$ and $C_4$ alkanes to aromatics. U.S. Pat. No. 4,528,412 discloses a catalyst employing gallium dispersed in moderate acidity, ZSM-5-type zeolites for this purpose. PEP Review 85-3-3, "Aromatics from LPG," provided by SRI International, also discusses uses for this catalyst. Catalysts for the dehydrocyclodimerization process are also disclosed by A. H. P. Hall in European Patent No. 162,636. U.S. Pat. No. 4,350,835 discloses the use of Ga/H-ZSM-5 for ethane conversion to aromatics. Very recently, U.S. Pat. No. 4,985,384 has disclosed gallium containing zeolite-Beta as a catalyst for increasing aromatic yields during fluid catalytic cracking. Gallium has also been noted as a component in light alkane dehydrogenation catalysts. U.S. Pat. No. 4,056,576 discloses gallium oxide, gallium sulfate, and gallium ions exchanged onto the surface of hydrated silica or hydrated alumina, optionally modified with Pt, Pd, In, Cr, Tl, Ge, Sn, or Zn. Selectivity for propane dehydrogenation to propylene over $Ga_2O_3/SiO_2$ at 610° C. was only 71.3%. British Patent No. 1,499,297 discloses dehydrogenation of $C_{10}+$ paraffins over catalysts containing platinum and gallium, indium, or thallium deposited on alumina together with minor amounts of lithium or potassium. Gallium loadings of 0.2 to 1.0 wt. % are suitable, loadings below 0.5 wt. % are preferred. Neither of these patents directly considers light paraffin dehydrogenation over bimetallic PtGa catalysts or the use of supports such as $MgAl_2O_4$ spinels. U.S. Pat. No. 4,902,849 discloses dehydrogenation of $C_2$-$C_5$ paraffins over catalysts comprising at least one aluminate spinel selected from the group consisting of aluminates of Group IIA metals and Group IIB metals, at least one metal selected from the group consisting of nickel, ruthenium, rhodium, palladium, osmium, iridium, and platinum, and at least one compound of a metal selected from the group consisting of germanium, tin, and lead. This patent does not consider the presence of Ga at all, nor is it drawn exclusively to magnesium alumina spinels.

SUMMARY OF THE INVENTION

The present invention relates to a process for the dehydrogenation of light paraffins, said process comprising the contacting of said light paraffins with a catalyst comprising Pt and Ga on a spinel support comprised of Mg and $Al_2O_3$.

BRIEF DESCRIPTION OF THE DRAWING

The sole figure compares the percentage of propane converted to olefins by various catalysts of the examples herein at specific exposure periods. The effectiveness of a commercial preparation is compared to compositions comprising Pt alone on a magnesium spinel support, Pt and Sn combined on a magnesium spinel support, and Pt and Ga combined on a magnesium spinel support.

DETAILED DESCRIPTION OF INVENTION

Aluminas suitable for use in accordance with the present invention are any of the high purity aluminas suitable for use as a support for reforming catalysts. The alumina can be synthetic or naturally occurring, although synthetic alumina is preferred because its preparation can be controlled to insure the appropriate level of purity and desired physical characteristics. It is also preferred that the alumina be one which upon calcination forms gamma alumina. By "an alumina which upon calcination forms gamma alumina" it is meant an alumina which is essentially in the trihydrate form prior to calcination, and which upon calcination is, according to the crystal pattern, gamma alumina. Principally, these aluminas are derived from precipitation methods or, preferably, the digestion of metallic aluminum by a weak organic acid.

In a preferred precipitation method, the alumina is prepared by the addition of an acid or acid salt such as hydrochloric acid or any of the alums, to an alkali metal aluminate, such as sodium or potassium aluminate.

The most preferred aluminas suitable for use herein are those prepared by digesting, or reacting, metallic aluminum with a weak organic acid to form an alumina sol. Preferred weak organic acids include acetic and formic acid. It is also preferred that the aluminum be digested in the presence of a mercury compound, such as a mercury aluminum hydroxide complex of acetic acid. Such processes are well known to those skilled in the art and are described in U.S. Pat. Nos. 2,274,634; Re 22,196 and 2,859,183; all of which are incorporated herein by reference. As previously mentioned, in such a process, an alpha aluminum salt is prepared by dissolving metallic aluminum in a dilute (about 1-6 wt. %) organic acid in the presence of a mercury compound. The aluminum and mercury form an amalgam which slowly dissolves with the evolution of hydrogen to alumina salt containing mercury, undissolved aluminum, and other materials. If desired, the resulting sol can be treated with a sufficient amount of ammonium hydroxide to obtain a pH of about 6.8 to 7.8, to form a gel which can be dried and calcined. It is preferred that the sol not be gelled, but that it be sprayed-dried to produce a high purity alumina hydrate powder, which can then be ground to an appropriate particle size. Although not critical for the practice of the present invention, an appropriate particle size is from about 5 to 15 microns.

The magnesium component can be incorporated into the alumina during any stage of the preparation of alumina as long as the mole ratio of Mg to alumina is about 0.1 to 1.1. In a particularly preferred production scheme for producing the alumina of this invention, high purity alumina hydrate powder is first prepared by digesting metallic aluminum in a weak organic acid, thereby forming an alumina sol which is then spray-dried by a conventional spray-drying technique to produce the alumina hydrate powder. If the alumina hydrate powder is not of appropriate particle size, it can be ground by a conventional grinding means for reducing the particle size of refractory powders. The alumina hydrate powder is then blended with an effective amount of water, or sol, to form a paste of sufficient consistency for extrusion.

Magnesium can be introduced into the alumina paste using a water soluble magnesium compound such as magnesium nitrate, magnesium acetate, etc. or as a finely divided hydrous oxide derivative of magnesium oxide such as "magnesium hydroxide" ($Mg(OH)_2 \cdot x H_2O$). After thorough mixing, the magnesium-containing alumina paste is then extruded into an appropriate shape such as cylindrical or trilobal pellets, dried and calcined for one to several hours at temperatures from about 400° C. to about 700° C. Calcination is preferably conducted at 600° C. to 700° C. Magnesium containing alumina supports produced in this manner preferably exhibit characteristic features in the X-ray powder diffraction pattern indicating partial or complete conversion of magnesium and aluminum to magnesia alumina spinel, $Mg_xAl_2O_{3+x}$, where x is a number from about 0.1 to 1.1, preferably about 1.

It is more preferred that the magnesium be incorporated by blending the alumina sol with a magnesium component, in the form of a water soluble salt, prior to spray drying. The magnesium component can also be mixed with the alumina powder prior to grinding. Although the magnesium component can concurrently be incorporated into the alumina hydrate material after extrusion by conventional impregnation techniques, it is preferred to introduce the magnesium component prior to extrusion to ensure homogeneity of the magnesium throughout the alumina material.

Suitable alumina supports can also be produced by extruding and calcining an alumina paste to form gamma alumina followed by impregnation of a soluble magnesium salt with drying and calcination at about 500° C. to 700° C. under conditions similar to those used to produce the alumina. This process is effective for depositing low concentrations of magnesium. However, multiple impregnations may be required to achieve, the preferred magnesium loadings depending on the pore structure and pore volume of the alumina used.

Another approach for producing suitable magnesium-alumina support materials has been reported by Rennard et al. (*Journal of Catalysis*, Vol. 98, Pg. 235, 1986) which involves coprecipitation of aqueous aluminum and magnesium nitrates at pH 10 using dilute $NH_4OH$ followed by filtration, drying at about 100° C. for about 18 hours, and finally air calcination at about 600° C. for about 18 hours.

The light alkane dehydrogenation catalysts of this invention are prepared by incorporating Pt and Ga, metals capable of providing a hydrogenation-dehydrogenation function, onto the $Mg_xAl_2O_{3+x}$ support. The Pt will be present on the catalyst in an amount from about 0.1 to 5 wt. %, calculated on an elemental basis, of the final catalyst composition. Preferably the catalyst contains from about 0.2 to about 1.0 wt. % Pt. The Ga content of the catalyst may range from about 0.3 wt. % to about 5 wt. %, preferably from about 0.5 to about 3 wt. % Ga, based on the total weight of the catalyst (dry basis). Gallium to platinum atomic ratios of 5 to 20 are preferred.

The Pt and Ga can be incorporated into the alumina by techniques such as by impregnation either before or after it has been pilled, pelleted, beaded or extruded. If impregnation is used, the modified alumina, in a dry or solvated state, is contacted or otherwise incorporated with a platinum and gallium salt and thereby impregnated by the "incipient wetness" technique. Platinum and gallium can be impregnated sequentially with intermediate drying and calcination or simultaneously. Simultaneous impregnation is preferred. The incipient wetness technique embodies absorption from a dilute or concentrated solution, with subsequent filtration or evaporation to effect the total uptake of the metallic components. The solution used in impregnation can be a salt or acid solution having the respective platinum and/or gallium compounds dissolved therein. Chloroplatinic acid and gallium nitrate are convenient precursors for catalyst preparation, although other water soluble platinum and gallium compounds such as $Pt(NH_3)_4(NO_3)_2$, $Pt(acetylacetanate)_2$, or gallium halides, acetates, etc. can be used with similar effectiveness. The impregnation treatment can be carried out under a wide range of conditions, including ambient or elevated temperatures, and atmospheric or superatmospheric pressures.

The catalyst may also contain a halide component which contributes to the acid functionality of the catalyst. The halide may be fluoride, chloride, iodide, bromide, or mixtures thereof. It is preferred that the halide be a chloride. Generally, the amount of halide is such that the final catalyst composition will contain from about 0.01 to about 3.5 wt. %, preferably less than about 0.5 wt. %, of halogen calculated on an elemental basis. The halogen can be introduced into the catalyst by any method at any time of the catalyst preparation, for example, prior to, following or simultaneously with the impregnation of the platinum. In the usual operation, the halogen component is introduced simultaneously with the incorporation of platinum. Halogen can also be incorporated by contacting the modified alumina in a vapor phase, or liquid phase, with a halogen compound such as hydrogen fluoride, hydrogen chloride, ammonium chloride, or the like.

The catalyst, after impregnation of Pt and Ga, is dried by heating to a temperature above about 27° C. preferably between about 65° C. and 150° C., in the presence of nitrogen or oxygen, or both, in an air stream or under vacuum. The catalyst can then be calcined at a temperature from about 300° C. to 650° C., preferably from about 400° C. and 600° C., in the presence of nitrogen or oxygen in an air stream, or in the presence of a mixture of oxygen and inert gas. This calcination, or activation, is conducted for periods ranging from about 1 to about 24 hours in either flowing or static gasses. Optionally, reduction is performed by contact with flowing hydrogen at temperatures ranging from about 175° C. to about 600° C. for periods ranging from about 0.5 to about 24 hours at about 1 to 10 atm. Moreover, the catalyst may optionally be sulfided by use of a blend of $H_2S/H_2$ at temperatures ranging from about 175° C. to about 500° C. at about 1 to 10 atm for a time necessary to achieve breakthrough, or until the desired sulfur level is reached. Post-sulfiding stripping can be employed, if desired, at conditions similar to those for reduction of the catalyst.

The alumina spinel materials of this invention are characterized as: (i) having a Mg to $Al_2O_3$ mole ratio of about 0.1 to 1.1; (ii) a surface area greater than about 50 $m^2/g$, preferably from about 125 to 200 $M^2/g$; (iii) a bulk density from about 0.6 to 0.9 g/ml, preferably from about 0.7 to 0.8 g/ml; (iv) an average pore volume from about 0.3 to about 0.7 ml/g, preferably from about 0.4 to about 0.5 ml/g; and (v) an average pore diameter from about 75 to 150 Å.

The feed, or charge stock can be selected from propane, normal butane, isobutanes, pentanes and other LPG (liquid petroleum gas) range saturated hydrocarbons. These hydrocarbons are extremely volatile. Propane boils within the range of about −46° C. to −38° C. at atmospheric pressure, and commercial butane boils at about 9.4° C.

The runs are initiated by adjusting the hydrogen and feed rates, and the temperature and pressure to operating conditions. The run is continued at optimum conditions by adjustment of the major process variables, within the ranges described below:

| Major Operating Variables | Typical Process Conditions | Preferred Process Conditions |
|---|---|---|
| Pressure, psia | 5–60 | 10–30 |
| Reactor Temp., °C. | 450–750 | 525–625 |
| $H_2$/Hydrocarbon Molar Feed Ratio | 0–1 | 0–0.5 |
| Feed Rate, GHSV* | 400–4000 | 600–2000 |

*(gas hourly space velocity = volume of gas per volume of catalyst per hour)

The instant invention is illustrated further by the following examples which, however, are not to be taken as limiting in any respect. All parts and percentages, unless expressly stated otherwise, are by weight.

EXAMPLES 1 and 2, and COMPARATIVE EXAMPLES A–E

A series of catalysts with comparable loadings of platinum, tin, indium, gallium, copper, lanthanum, and palladium was prepared using incipient wetness impregnation methods employing aqueous $H_2PtCl_6$, $SnCl_2$, $In(NO_3)_3$, $Ga(NO_3)_3$, $Cu(NO_3)_2$, $La(NO_3)_3$, and $Pd(NH_3)_4(NO_3)_2$. The support materials used in these studies were a reforming high grade purity alumina along with a magnesium alumina spinel ($MgAl_2O_4$) that was produced by coprecipitating aqueous aluminum and magnesium nitrate (in a molar ratio of 2:1) at pH 10 at ambient temperature using $NH_4OH$. This was followed by drying at 100° C. for 18 hours, and calcinated at 600° C. for 18 hours. This series of catalysts was produced by sequential impregnation of Pt or Pd followed by impregnation of Sn, In, Ga, Cu or La as indicated. After each metals impregnation step, the catalysts were dried in air, then in vacuum at 100° C., and finally calcined in air at 600° C. for 18 hours.

The catalysts were evaluated for dehydrogenation activity in a small downflow microreactor using a 1.5 g charge of nominally 14/35 mesh catalyst and a feed gas blend of propane/hydrogen in a 3.3/1 molar ratio. Standard conditions for the reaction studies were 605° C., 1 atm total pressure, and 65 cc/minute gas feed rate (e.g., ca. 2000 GHSV (gas hourly space velocity=volumes of gas per volume of catalyst per hour), 2 second contact time). Activation was accomplished by hydrogen reduction for 1 hour at 500° C. followed by heating in flowing hydrogen to 600° C. prior to introducing propane.

Table I below summarizes catalytic data obtained after 40–100 minutes on feed for the above catalysts. Propane conversion and propylene selectivity have been used as primary indicators of performance. Propylene selectivity represents the fraction (percentage) of reacting propane molecules which produce propylene.

Several features should be noted from Table I. For example, 0.6 wt. % Pt on $MgAl_2O_4$ showed respectable performance characterized by moderate activity and selectivity, whereas palladium only showed poor activity. A catalyst containing 2.5 wt. % Ga on MgAl$_2$O$_4$ also showed significant intrinsic activity for dehydrogenation along with very high 95% selectivity. However, The combination of 0.6 wt. % platinum with 2.5–5.0 wt. % gallium produced exceptional catalysts with very high activity and dehydrogenation selectivities. The improved selectivity achieved relative to catalysts based on the individual components clearly appears to suggest a synergistic interaction between platinum and gallium.

No performance credits were realized with a high gallium loading indicating that the optimum gallium/platinum atomic ratio is somewhat less than 20. Combining 0.6 wt. % platinum with other additives such as copper or lanthanum produced changes in activity and selectivity, although none of these catalysts displayed performance approaching that of the platinum-gallium systems. It is also notable that the PdGa/MgAl$_2$O$_4$ catalyst displayed inferior performance relative to PtGa/MgAl$_2$O$_4$.

with novel and special properties. It is noteworthy that the PtGa catalyst is particularly superior to PtSn, since the latter material is thought to be similar in terms of metals composition to the platinum-tin catalysts employed in commercial light alkane dehydrogenation technologies. It is also important to note by comparison of reaction data collected at 10 minutes and 100 minutes, that the PtGa catalyst displayed the lowest rate of deactivation among the materials studied.

TABLE II

Catalytic Behavior of Platinum in Combination with Tin, Indium, and Gallium

| Examples | Catalyst | Propane Conversion[2] (% at time on stream) | | Propylene Selectivity[2] (% at time on stream) | |
|---|---|---|---|---|---|
| | | 10 Min. | 100 Min. | 10 Min. | 100 Min. |
| Comp. F | 0.3 Pt/MgAl$_2$O$_4$ | 15 | 8 | 76 | 82 |
| Comp. G | 0.3 Pt-1.0 Sn/MgAl$_2$O$_4$ | 21 | 11 | 91 | 90 |
| Comp. H | 0.3 Pt-1.0 In/MgAl$_2$O$_4$ | 19 | 13 | 95 | 96 |
| 3 | 0.3 Pt-1.0 Ga/MgAl$_2$O$_4$ | 30 | 27 | 95 | 96 |

[2]@ 605° C., C3/H2 = 3.3, 1 atm, 2000 GHSV

EXAMPLE 4 and COMPARATIVE EXAMPLES I–O

To gain further insight into the performance of PtGa/MgAl$_2$O$_4$ relative to other materials, comparisons were carried out. One material used was a catalyst comprising 0.3 wt. % Pt and 0.3 wt. % Re on Al$_2$O$_3$ (Comp. Ex. I) prepared by loading with 3% potassium using incipient wetness impregnation of KNO$_3$, prior to calcination and sulfiding. A second catalyst comprised 0.8 wt. % Pt on K-L zeolite (Comp. Ex. J) and a third catalyst contained 2.7 wt. % chromium and 0.5 wt. %

TABLE I

Catalytic Behavior of Several Materials for Propane Dehydrogenation

| Examples | Catalyst | Propane Conversion[1] % at time on stream | | Propylene Selectivity[1] % at time on stream | |
|---|---|---|---|---|---|
| | | 40 Min. | 100 Min. | 40 Min. | 100 Min. |
| Comp. A | 0.6 Pt/MgAl$_2$O$_4$ | 20 | 17 | 84 | 87 |
| Comp. B | 0.5 Pd/MgAl$_2$O$_4$ | 3 | 3 | 71 | 72 |
| Comp. C | 2.5 Ga/MgAl$_2$O$_4$ | 16 | 16 | 96 | 95 |
| 1 | 0.6 Pt-2.5 Ga/MgAl$_2$O$_4$ | 33 | 31 | 98 | 98 |
| 2 | 0.6 Pt-5.0 Ga/MgAl$_2$O$_4$ | 31 | 30 | 97 | 98 |
| Comp. D | 0.6 Pt-2.5 Cu/MgAl$_2$O$_4$ | 20 | 18 | 93 | 94 |
| Comp. E | 0.6 Pt-2.5 La/MgAl$_2$O$_4$ | 12 | 10 | 28 | 90 |
| Equilibrium for conditions | | | 37 | | 100 |

[1]@ 605° C., C3/H2 = 3.3, 1 atm, 2000 GHSV

EXAMPLE 3 and COMPARATIVE EXAMPLES F–H

In order to better assess the behavior of catalysts containing platinum in combination with elements from Group III and Group IV, a series of catalysts was prepared containing 0.3 wt. % platinum and 1.0 wt. % indium, tin, and gallium. As indicated in Table II below, addition of tin and indium moderately improved the activity and selectivity of the base platinum catalyst. However, none of these catalysts showed activity approaching that of the platinum-gallium catalyst of the present invention. Thus, it appears evident that the combination of platinum and gallium produces catalysts potassium (Comp. Ex. M) dispersed on alumina. The latter material was prepared to simulate the properties of the classic Houdry-type catalyst described in U.K. Patent Application BG 2162082A. A commercial CrK/Al$_2$O$_3$ dehydrogenation catalyst containing about 4% chromium was also evaluated. As indicated in Table III, all of these catalysts exhibited initial propane conversion activity that was comparable to that of PtGa-catalysts. However, none of these catalysts exhibited the high dehydrogenation selectivities afforded by PtGa/MgAl$_2$O$_4$ providing further evidence for the special and superior performance of this system. Moreover, the PtGa/MgAl$_2$O$_4$ catalysts showed reduced deactivation rates relative to the other materials.

TABLE III

Catalytic Behavior for Propane Dehydrogenation

| Example | Catalyst | Propane Conversion[3] (% at time on stream) | | Propylene Selectivity[3] (% at time on stream) | |
| --- | --- | --- | --- | --- | --- |
| | | 40 Min. | 100 Min. | 40 Min. | 100 Min. |
| Comp. I | Sulfided 0.3 Pt-0.3 Re/Al$_2$O$_3$ | 39 | 28 | 84 | 82 |
| Comp. J | Sulfided 3 K/0.3 Pt-0.3 Re/Al$_2$O$_3$ | 39 | 23 | 88 | 88 |
| Comp. K | 0.8 Pt/K-L zeolite | 52 | 40 | 44 | 49 |
| Comp. L | 2.5 Cr/MgAl$_2$O$_4$ | 24 | 21 | 95 | 94 |
| Comp. M | 2.7 Cr-0.5 K/Al$_2$O$_3$ | 26 | 32 | 92 | 91 |
| Comp. N | Commercial CrK/Al$_2$O$_3$ | 43 | 78 | 27 | 90 |
| Comp. O | 2.5 Ga-2.7 Cr-0.5 K/Al$_2$O$_3$ | 37 | 34 | 92 | 91 |
| 4 | 0.3 Pt-1.0 Ga/MgAl$_2$O$_4$ | 30 | 27 | 95 | 96 |
| 5 | 0.6 Pt-2.5 Ga/MgAl$_2$O$_4$ | 33 | 31 | 98 | 98 |

[3]@ 605° C., 1 atm, 2000 GHSV, C$_3$/H$_3$ = 3.3

EXAMPLE 5

As noted above, the PtGa/MgAl$_2$O$_4$ catalysts consistently exhibited superior activity maintenance as compared to the other materials investigated. This is shown more clearly in the Figure, which compares propane conversion as a function of reaction time at 605° C. for five catalysts with different compositions.

EXAMPLE 6

Studies were also conducted using isobutane as a light alkane feedstock at 575° C., 1 atm, GHSV=2400, and with a molar C$_4$H$_{10}$/H$_2$ feed ratio of 3.0. Very stable activity and dehydrogenation selectivity were observed with the 0.6% Pt-2.5% Ga/MgAl$_2$O$_4$ catalyst over a period of 22 hours. At the end of this period, the catalyst was subjected to a simulated air regeneration test by treatment with air at 500° C. and with GHSV=1500 for 2 hours. Subsequently, the isobutane reaction was restarted. Table IV compares performance data for isobutane dehydrogenation in the first and second reaction cycles. The data indicate that PtGa/MgAl$_2$O$_4$ is a robust catalyst that can withstand a high temperature air treatment aimed at removal of coke deposits. Moreover, these data clearly show that PtGa/MgAl$_2$O$_4$ is a very effective catalyst for butane dehydrogenation.

TABLE IV

Isobutane Dehydrogenation Results

| Cycle | Time on Feed (hours) | Isobutane Conversion[4] (mole %) | Isobutene Selectivity[4] (mole %) |
| --- | --- | --- | --- |
| 1 | 1 | 41 | 95 |
| 1 | 21 | 41 | 96 |
| — | air treat | | |
| 2 | 1 | 43 | 95 |
| 2 | 6 | 37 | 97 |

[4]@ 575° C., 240 GHSV, 1 atm

What is claimed is:

1. A process for the dehydrogenation of light paraffins, said process comprising contacting of said light paraffins under dehydrogenation conditions with a catalyst consisting essentially of Pt and Ga on a Mg aluminate spinel having the formula Mg$_x$Al$_2$O$_{3+x}$, where x is a number from about 0.1 to 1.1.

2. The process of claim 1, wherein said catalyst contains a halide component.

3. The process of claim 2, wherein said halide is chloride and wherein said catalyst is sulfided.

4. The process of claim 1, wherein the Ga content is from about 0.3 to about 5 wt. % and the Pt content is from about 0.1 to 5 wt. %, and the spinel support material comprises Mg and Al$_2$O$_3$ in a mole ratio of from about 1 to 1.

5. The process of claim 4, wherein said catalyst comprises from about 0.5 to about 3 wt. % Ga and Pt is present in a range from about 0.2 to about 1.0 wt. % Pt.

6. The process of claim 4, wherein said catalyst contains a halide and has been sulfided.

7. A process for the dehydrogenation of light paraffins, said process comprising contacting said light paraffins under dehydrogenation conditions with a catalyst consisting essentially of Ga and Pt supported upon an magnesium aluminate spinel, wherein said catalyst is made in a procedure comprising the steps:
   (a) incorporating Mg into an Al$_2$O$_3$ support material in a mole ratio of Mg to Al$_2$O$_3$ of from about 0.1 to 1.1;
   (b) calcining said support material for an effective amount of time at an effective temperature to form a magnesium aluminate spinel material;
   (c) incorporating about 0.3 to about 5 wt. % Ga and 0.1 to 5 wt. % Pt into said calcined spinel material.

8. The process of claim 7, employing a catalyst wherein Mg is incorporated into said alumina support material prior to shaping the support.

9. The process of claim 1, which operated at a pressure of between 5 and 60 psia, a temperature between 450° and 750° C., a hydrogen to oil ratio maintained at 1 or below, and a feed rate, gas hourly space velocity of from 400 to 4000.

10. The process of claim 9, which is operated at a pressure between 10 and 30 psia, a temperature between 525° and 625° C., a hydrogen to oil ratio maintained at 0.5 or below, and a feed rate, gas hourly velocity of from 600-2000.

11. The process of claim 10 wherein said light paraffins comprise propane, normal butane, isobutanes, pentanes and other saturated hydrocarbons from the liquid petroleum gas range.

* * * * *